United States Patent [19]

Sanchez

[11] 4,386,933
[45] Jun. 7, 1983

[54] STERILE ADAPTER FOR USE IN BLOOD TRANSFERS

[76] Inventor: Enrique R. Sanchez, 226 E. 13 St., Hialeah, Fla. 33010

[21] Appl. No.: 266,110

[22] Filed: May 21, 1981

[51] Int. Cl.³ .............................................. A61J 1/00
[52] U.S. Cl. .................................. 604/408; 604/905; 285/137 R
[58] Field of Search ................ 128/272, 272.3, 214 D, 128/214.2, 247, 214 C; 285/132, 137 R, 3, 4; 141/19, 329, 330, 383–386; 222/83, 83.5, 85, 86; 604/408, 411, 414, 905

[56] References Cited

U.S. PATENT DOCUMENTS 3,902,489  9/1975  Carter ...................................... 285/3
4,022,205  5/1977  Tenczar .................................. 285/3

FOREIGN PATENT DOCUMENTS 1082035  12/1954  France .

Primary Examiner—Richard J. Apley
Assistant Examiner—J. L. Kruter
Attorney, Agent, or Firm—John Cyril Malloy

[57] ABSTRACT

A sterile entry system for use in transferring blood from a unit of blood to a transfer bag wherein the transfer bag is provided with a cannula extending from a disc of predetermined size and the unit of blood includes an access port defining structure and the sterile entry system comprises a sleeve having an open end sized to snugly jacket the exterior periphery of the disc and a closed end, a base spanning the end, and the base having an upper surface within the sleeve and a lower surface exterior of the sleeve and the base including a through bore extending between the surfaces, the through bore having seal means spanning the opposite ends thereof and the seal means being adapted to be pierced.

5 Claims, 3 Drawing Figures

STERILE ADAPTER FOR USE IN BLOOD TRANSFERS

FIELD OF THIS INVENTION

This invention relates to devices used by blood banks and transfusion services. More particularly this invention relates to a device for use in transferring blood from a blood storage unit to a transfer container or bag.

BACKGROUND OF THE INVENTION

In the past there have been numerous types of devices which are utilized for handling blood. It will be appreciated that it is important that the blood be maintained in a sterilized condition. For this reason, there is, generally speaking, a rule that blood which is transferred through what is known as an open system from a blood storage unit to a transfer bag must be utilized within twenty-four hours. This is because the cannula is exposed to air and its tip is utilized to pierce into the storage unit of blood through a seal, which hermetically seals the blood storage unit. This is so that there is not sufficient time for objectionable amounts of bacteria to grow. This means that blood, a precious commodity, is often wasted because it cannot be used within the time limit prescribed.

This is an invention which avoids that problem in that it maintains the cannula and more particularly the piercing tip of the cannula in a sterilized environment.

This invention consists of a sleeve having a base which has an upper surface and a lower surface and wherein the cannula tip is arranged within the sleeve, which is of flexible pliable material and adapted to be advanced into piercing engagement with a pair of seals closing the upper surface of the base at a bore mouth and this bore has its lower end sealed to be pierced by a port access defining structure on the unit of blood. Generally speaking, this invention can be utilized to maintain the cannula tip in a sterilized condition so that the transfer of blood may take place without exposing it to the deliterious effects of air and, hence, avoid the problem of waste because the time limit does not apply. Since blood has an expiration date of up to a month or longer, oftentimes determined to be thirty-five days, it will be appreciated that the length of time within which the blood may be utilized without the necessity for throwing it away is prolonged immeasurably and, hence, this precious commodity is not wasted.

OBJECTS OF THIS INVENTION

Accordingly, it is an object of this invention to provide a device of the type described which is suitable for use in transferring blood from a blood storage unit to a transfer bag and, simultaneously, maintaining the cannula tip, which is conventionally employed in such devices, in a sterilized condition and wherein a sleeve is provided in surrounding relation of the cannula tip and which sleeve is collapsible so that the cannula tip, which is conventionally pointed, may be utilized to pierce a seal which is provided in the base of the invention.

In accordance with these and other objects which will become apparent hereinafter, the instant invention will now be described with reference to the accompanying drawings in which:

DESCRIPTION OF THE PREFERRED EMBODIMENT

Figure 1:
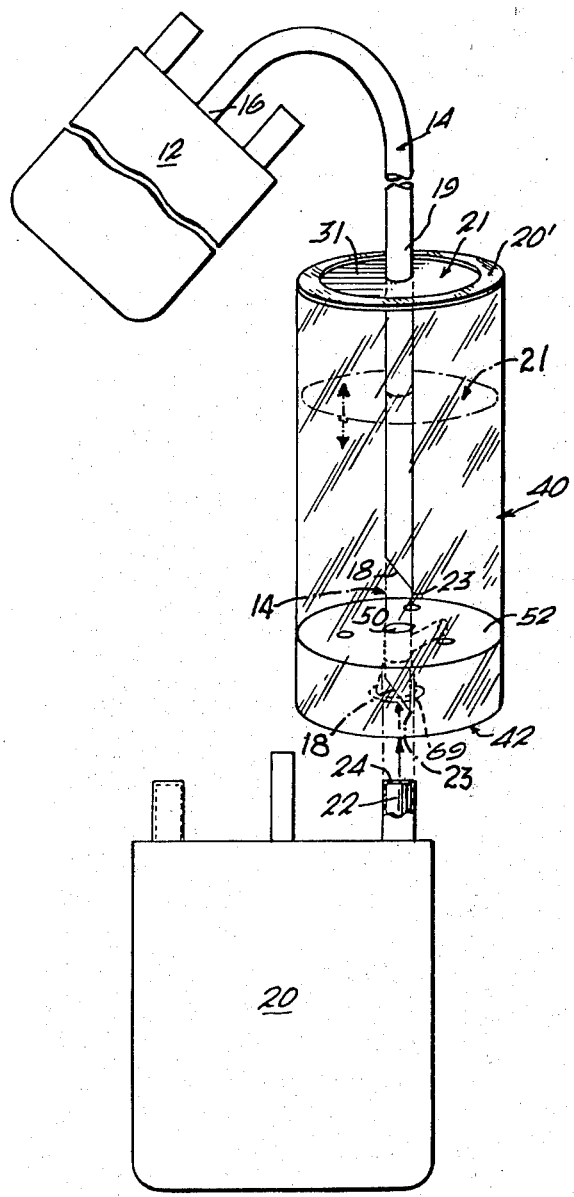
FIG. 1 is an exploded perspective view of the sterile adapter of the present invention connected to a blood transfer bag with a second bag containing blood to be transferred and showing in phantom lines how the cannula tip can pierce the seal of the sterile adapter of the invention.

Referring to FIG. 1, there is shown a transfer bag generally designated by the numeral 12 and, as is conventional, it includes a piece of tubing or cannula 14 which is connected at one end 16 to the transfer bag 12 and which leads to a sharpened end 18. This is conventional. In the prior art it is utilized with a bag of blood such as that designated by the numeral 20. Conventionally, such bags of blood have an access port defining structure 22 extending upwardly from one end and, normally, this is provided with a flexible plastic film seal 24. In use, the sharpened end 18 is inserted into the access port structure 22 and in so doing, the plastic seal 24 is pierced. This is known as an open system because the tip 18 of the cannula is exposed to the air. In practice, blood utilizing this system which is transferred from the unit 20 to the transfer bag 12 can only be kept for use within twenty-four hours after the transfer. If not, it must be discarded. This invention is of the sleeve which is generally designated by the numeral 40 and which has a base 42 to be described.

Figure 2:
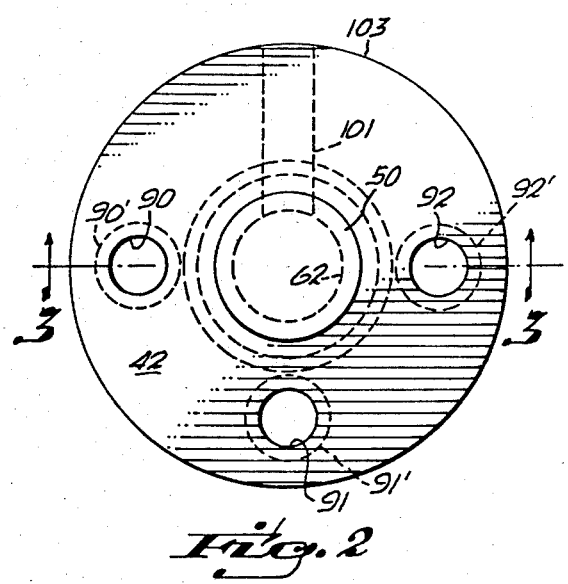
FIG. 2 is a top plan view of the base portion of the adapter.
Figure 3:
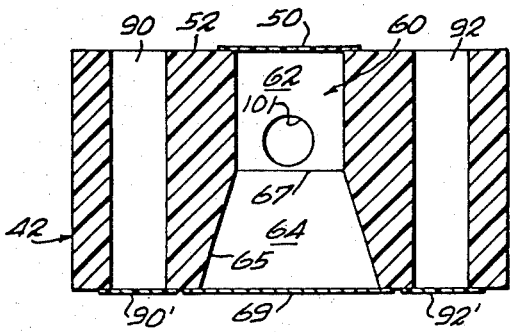
FIG. 3 is a cross sectional view taken along line 3—3 of FIG. 2.

Briefly, on the cannula intermediate length as at 19 there is conventionally a disc 21. This disc is of a predetermined diameter. The sleeve 40 of this invention is provided with an inside diameter which closely jackets the exterior periphery of disc 21. In use of this invention, the disc 21 and the intermediate portion 19 are pushed downwardly so that the pointed tip 23 pierces a seal 50 on the top surface 52 of the base 42. Reference will now be made to FIGS. 2 and 3 wherein the base generally designated by the numeral 42 is seen to have a bore 60 therethrough with an upper end 62 and a lower end 64, the lower end being somewhat larger than the upper end 62 and provided with a tapered wall 65 to the juncture 67. A seal 69 is provided at the lower end which may be of aluminum. The base 42 is positioned over the access port structure 22 of the unit 20 piercing this aluminum seal. Thereafter, when the tip 23 of the cannula is advanced it will pierce the seal which is provided in the top as at 50 of the base closing the end 62 of the bore breaking through this and permitting the blood to be transferred through the bore and the cannula.

In the preferred embodiment, the base is provided with a plurality of openings such as 90, 91, and 92 which extend therethrough and, when sterilized, the sterilizing medium can enter through these ports into the interior of the sleeve. When this process has been completed, these bores are capped by the circular seals generally designated by the numerals 90', 91' and 92'.

It is thus seen that this adapter composed of the sleeve of a diameter sized to snugly receive the disc and the attached base provide for a sterile entry system whereby blood may be transferred to a transfer bag 12 from a unit 20. There is a port 101 extending from the outer surface 103 of the base to the bore 62 so that sterilizing gas may enter into and sterilize the base.

In a preferred embodiment the sleeve will be of flexible pliable material and preferably have a mouth at the upper end sized to snugly receive the disc and having a marginal end or end zone 20' which is adapted to be folded over onto the surface 31 of the disc and be adhered thereto by suitable means, such as bonding or adhesive.

While this device has been described for use in connection with a sterile entry system for transferring blood, it will be appreciated that other fluids in a medical setting may also be transferred, such as saline solutions, dextrose solutions and the like.

While the instant invention has been shown and described herein in what is conceived to be the most practical and preferred embodiment, it is recognized that departures may be made therefrom within the scope of the invention, which is therefore not to be limited to the details disclosed herein but is to be accorded the full scope of the claims so as to embrace any and all equivalent apparatus and articles.

What is claimed is:

1. A sterile entry system for transferring blood from a unit of blood to a transfer bag, the transfer bag including a cannula means extending through a disc, a unit of blood including an access-port-defining structure, said sterile entry system comprising a sleeve having a longitudinally extending axis, an upper open end snugly jacketing the exterior periphery of said disc for sliding longitudinal movement of said disc and canula means within said sleeve, said sleeve including a lower end closed by a base spanning said lower end, said base having an upper surface within the sleeve and a lower surface exterior of the sleeve, said base including a through bore between said surfaces, seal means spanning opposite ends of said through bore at the respective upper and lower surfaces, said seal means being rupturable by said cannula means when said cannula means is moved longitudinally within said sleeve and through said through bore.

2. The device as set forth in claim 1 wherein said sleeve is of flexible pliable plastic material.

3. The device as set forth in claim 1 wherein said sleeve includes an upper marginal edge and said marginal edge is adapted to be folded over onto the surface of the disc and secured thereto.

4. The device as set forth in claim 1 wherein said base includes a plurality of spaced ports extending and communicating between the surfaces providing a means for introducing a sterilizing medium into the sleeve.

5. The device as set forth in claim 4 wherein said base includes a generally radially extending port extending from the exterior peripheral surface of the base between the upper surface and the lower surface and in fluid communication with said through bore.

* * * * *